United States Patent
Emler

(10) Patent No.: US 8,275,557 B2
(45) Date of Patent: Sep. 25, 2012

(54) COMPUTER-IMPLEMENTED METHOD AND COMPUTER-BASED SYSTEM FOR VALIDATING DNA SEQUENCING DATA

(75) Inventor: Stefan Emler, Zürich (CH)

(73) Assignee: SmartGene GmbH, Zug (CH)

( * ) Notice: Subject to any disclaimer, the term of this patent is extended or adjusted under 35 U.S.C. 154(b) by 1039 days.

(21) Appl. No.: 11/883,141

(22) PCT Filed: Feb. 11, 2005

(86) PCT No.: PCT/CH2005/000079
§ 371 (c)(1),
(2), (4) Date: Jul. 26, 2007

(87) PCT Pub. No.: WO2006/084391
PCT Pub. Date: Aug. 17, 2006

(65) Prior Publication Data
US 2008/0120079 A1    May 22, 2008

(51) Int. Cl.
*G01N 33/48* (2006.01)
(52) U.S. Cl. ......................................................... 702/20
(58) Field of Classification Search ...................... 702/20
See application file for complete search history.

(56) References Cited

U.S. PATENT DOCUMENTS

2005/0221354 A1* 10/2005 Mounts .............................. 435/6

OTHER PUBLICATIONS

Gleizes et al., "A global approach for contig construction", Computer Applications in the Biosciences, vol. 10, No. 4, pp. 401-408, 1994, Oxford University Press.
Herron-Olson et al., "MGView: an alignment and visualization tool to enhance gap closure of microbial genomes", Nucleic Acids Research, vol. 31, No. 17, pp. e106.1-e106.6, Sep. 1, 2003, Oxford University Press.
Bonfield et al., "A new DNA sequence assembly program", Nucleic Acids Research, vol. 23, No. 24, pp. 4992-4999, 1995, Oxford University Press.
Allex et al., "Neural network input representations that produce accurate consensus sequences from DNA fragment assemblies", Bioinformatics, vol. 15, No. 9, pp. 723-728, Sep. 1999, Oxford University Press.
Myers, Gene, "Whole-Genome DNA Sequencing", Computing in Science and Engineering, vol. 1, No. 3, pp. 33-43, May 1999, IEEE.
Z. Zhang et al., "A Greedy Algorithm for Aligning DNA Sequences", J Comput Biol 2000; 7(1-2):203-14.
W. Pearson ,"Using the FASTA Program to Search Protein and DNA equence Databases," Methods Mol Biol. 1994; 29:365-389.
Written Opinion of the International Searching Authority PCT/CH2005/000079 dated Aug. 14, 2007.

* cited by examiner

*Primary Examiner* — Jerry Lin
(74) *Attorney, Agent, or Firm* — Sughrue Mion, PLLC

(57) ABSTRACT

To validate DNA sequencing data from sequence data of one or more DNA fragments, a server (3) obtains a target specification from a user via a telecommunications network (2). From a set of one or more possible reference sequences (42), related to the target specification and stored in a database (4), the server (3) selects the reference sequence having the highest correlation with the fragment sequence data. For example, if the target specification identifies a gene sequence, then the reference sequence is selected from a set of variants of the gene sequence. Automatically, the server (3) aligns the fragment sequence data with the selected reference sequence and identifies any sequence positions where nucleotide codes of aligned fragment sequence data and selected reference sequence do not correspond. For validating DNA sequencing data, selection of reference sequence and identification of ambiguous nucleotide codes can be performed without human intervention, thus, the speed and reliability of the validation process is improved.

24 Claims, 4 Drawing Sheets

COMPUTER-IMPLEMENTED METHOD AND COMPUTER-BASED SYSTEM FOR VALIDATING DNA SEQUENCING DATA

FIELD OF THE INVENTION

The present invention relates to a computer-implemented method and a computer-based system for validating DNA sequencing data. Specifically, the present invention relates to a computer-implemented method and a computer-based system for validating the DNA sequencing data from sequence data of one or more DNA fragments (fragment sequence data). The present invention relates also to a computer program product for controlling the computer-based system such that the system executes the method of validating DNA sequencing data.

BACKGROUND OF THE INVENTION

Sequencing of DNA (Deoxyribonucleic Acid) is the determination of the precise sequence of nucleotides in a sample of DNA. The most common method for DNA sequencing was developed by Frederick Sanger and is referred to as the Dideoxy method or Sanger sequencing. The dideoxy method makes possible DNA sequencing based on sequencing of DNA fragments. Today, automated sequencers are used to generate computer-readable sequence data from DNA fragments. In its raw form, the sequence data includes electropherograms. An electropherogram includes an electropherographic signal for each of the four types of nucleotides (A Adenine, C Cytosine, G Guanine, and T Thymine). From amplitude peaks in the electropherographic signals, codes (A, C, G, T) can be derived for the types of nucleotides. In addition to the electropherographic signals, the sequence data from a sequencer may also include the encoded sequence of the DNA fragment, i.e. a sequence of codes of the derived nucleotide types. Typically, the sequences are validated through human intervention by an experienced lab technician, for example. For validation, the sequence of a DNA fragment is compared to a suitable reference sequence. For that purpose, the human operator must first search and retrieve "manually" a reference sequence from a database. Subsequently, the human operator compares visually the sequence of a DNA fragment to the reference sequence by checking nucleotide by nucleotide the correspondence of the respective nucleotide codes. Manual search, selection, and retrieval of reference sequences are time consuming and provide no guarantees that a reference sequence is selected optimally. There may very well exist a more suitable reference sequence providing a better match to the multiple sequences of DNA fragments to be validated and, therefore, helping to save time and reduce errors. Moreover, the search and selection of a reference sequence by a human operator is error prone as human and manual interventions take place.

SUMMARY OF THE INVENTION

It is an object of this invention to provide a computer-implemented method and a computer-based system for validating DNA sequencing data from sequence data of one or more DNA fragments (herein also referred to as "fragment sequence data"), which system and method do not have the disadvantages of the prior art. In particular, it is an object of the present invention to provide a computer-implemented method and a computer-based system for validating the DNA sequencing data from fragment sequence data, which system and method do not require human intervention for searching, selecting, and retrieving a reference sequence for validating the sequence data. It is a further object of the present invention to provide a computer-implemented method and a computer-based system for validating the DNA sequencing data from fragment sequence data, which system and method do not require human intervention for identifying ambiguous coding of nucleotides in the sequence data of the DNA fragments.

According to the present invention, these objects are achieved particularly through the features of the independent claims. In addition, further advantageous embodiments follow from the dependent claims and the description.

According to the present invention, the above-mentioned objects are particularly achieved in that, for validating the DNA sequencing data from fragment sequence data of one or more DNA fragments, i.e. for validating the sequences resulting from a sequencer "base-calling", a target specification is obtained from a user. A selected reference sequence, having a highest correlation with the sequence data of one or more than one sequenced fragments, is identified and is selected automatically from a set of one or more possible reference sequences, related to the target specification and stored in a database. The fragment sequence data is aligned automatically with the selected reference sequence. Reverse-complement orientation is adjusted with regard to the selected reference sequence. Automatically identified are sequence positions where nucleotide codes of aligned fragment sequence data and selected reference sequence do not correspond. Validation from sequence data of one or more DNA fragments with automatic selection of the reference sequence, based on assessing the level of correlation (i.e. the degree of pattern matching) between reference sequence and the fragment sequence data of one or more DNA fragments, has the advantage that no human intervention is required in the selection process. This increases the quality of the selection because there are no operating errors and because a best matching reference sequence is selected, through maximization of the correlation between the reference sequence and the sequence data of the DNA fragments. Using a computer for selecting the reference sequence makes it possible to use a high number of available reference sequences, thereby, increasing the likelihood of good matches. Furthermore, based on the selected reference sequence, it is made possible to detect and locate without any human interventions non-corresponding nucleotide codes in the fragment sequence data. Compared to "manual" selection and validation by an operator, the processing time for validating (or proofreading) DNA sequencing data is significantly reduced, while the quality is improved substantially.

In a preferred embodiment, a server obtains the target specification from the user via a telecommunications network and the server selects the selected reference sequence from the database. For example, the target specification identifies a gene sequence and the selected reference sequence is selected by the server from the database from a set of one or more variants of the gene sequence. Implementing the selection process on a network-based server makes it possible to provide efficiently (in terms of performance and financial costs) automatic selection of reference sequences as a centralized service, available to a plurality of users connected to the telecommunications network.

In a further preferred embodiment, a contig is generated as a consensus sequence from all the fragment sequence data aligned with the selected reference sequence. At sequence positions having non-corresponding nucleotide codes in the fragment sequence data, a special code indicating ambiguity (e.g. an IUPAC code) is inserted into the consensus sequence. In an embodiment, a contig is generated as a consensus sequence from the selected reference sequence and from the fragment sequence data aligned with the selected reference sequence. At sequence positions with corresponding or missing nucleotide codes in the fragment sequence data, a nucleotide code of the selected reference sequence is copied into the consensus sequence. Generating the contig from the sequence data of the DNA fragments and the reference sequence makes it possible to provide a continuous sequence even when the fragment sequence data leaves undefined sections of the sequence. Marking automatically sequence positions where overlapping sequences of DNA fragments have non-corresponding nucleotide codes makes it possible to reduce significantly the time needed for validating the sequence data. A human operator, i.e. the user, can navigate quickly and exclusively to sequence positions having non-matching nucleotide codes in the aligned sequences.

Preferably, sections of aligned fragment sequence data and selected reference sequence are displayed side by side. The sequence data of each DNA fragment is displayed along a separate line. Sequence positions with non-corresponding nucleotide codes are indicated visually in the sections. From the user obtained are instructions to modify a nucleotide code at sequence positions having non-corresponding nucleotide codes. The nucleotide codes are modified according to the instructions obtained from the user. Displaying the aligned sequences of DNA fragments and the reference sequence side by side and along separate lines makes possible very efficient and easy visual comparison of the fragment sequence data and the reference sequence. Visual marking of sequence positions with non-corresponding nucleotide codes further facilitates efficient locating of ambiguous sequence positions and subsequent editing (altering) of nucleotide codes.

In a variant, information about user-modified nucleotide codes are stored. Selectively, modified sections of aligned fragment sequence data and selected reference sequence, containing user-modified nucleotide codes, are displayed side by side. The user-modified nucleotide codes are indicated visually in the modified sections. Storing information such as DNA fragment identifier, sequence position, previous value, and user identifier of the human operator having performed the alteration, has the advantage that modifications in the fragment sequence data (and/or in the contig) can be located and reviewed at a later point in time.

In a further embodiment, sequence masks are stored in the database assigned to the reference sequences. The sequence masks each include profile information related to one or more positions of the respective reference sequence. Interest information is obtained from the user. Selected sections of aligned fragment sequence data and selected reference sequence are displayed side by side. The selected sections are determined based on the interest information obtained from the user and the profile information included in the sequence mask assigned to the selected reference sequence. Predefined masks specific to reference sequences make it possible to locate and navigate automatically to user specified areas of interest in the display showing the aligned fragment sequence data, reference sequence, and contig. Hence known critical and/or interesting sequence areas of a DNA sequence can be located selectively and efficiently.

In a variant, each of the sequence masks is stored in the database assigned to a user identifier and the selected sections are determined based on the sequence mask assigned to a user identifier obtained from the user. User-specific masks make it possible for different users or groups of users to define and associate different profile information with reference sequences.

In another preferred embodiment, the fragment sequence data includes electropherographic signals. Sections of aligned fragment sequence data and selected reference sequence are displayed side by side, the sequence data of each DNA fragment being displayed along separate lines as a sequence of nucleotide codes and as an electropherographic signal. The signal levels of the electropherographic signals are adjusted individually for the different nucleotide types based on settings obtained from the user. Displaying aligned fragment sequence data side by side as code sequences and as electropherographic signals has the advantage that the nucleotide codes can be compared directly to the corresponding electropherographic signals. Through adjusting signal levels of the electropherographic signals, the comparison of electropherographic signals to corresponding nucleotide codes can be made easier and clearer for the user.

In an embodiment, the fragment sequence data is generated by a sequencer and loaded via a telecommunications network to the server. Preferably, the server performs the steps of aligning the fragment sequence data and the selected reference sequence, generating the contig as a consensus sequence, and storing the contig in a database assigned to the fragment sequence data, the selected reference sequence, a user identifier obtained from the user, and information about user-modified nucleotide codes. Preferably, the aligned fragment sequence data and selected reference sequence are displayed on a display located at the user. Furthermore, through a data entry terminal located at the user, the instructions for setting in the contig a nucleotide code are obtained from the user.

In addition to a computer-implemented method and a computer-based system for validating the DNA sequencing data from sequence data of one or more DNA fragments, the present invention also relates to a computer program product including computer program code means for controlling one or more processors of the computer-based system such that the system executes the method of validating DNA sequencing data based on sequence data of one or more DNA fragments. Particularly, a computer program product including a computer readable medium containing therein the computer program code means (e.g. programmed software modules, as described later in more detail). Using a server-based technology for validating the DNA sequencing data makes it possible for a user to use its own computer equipment without having to install any software or hardware. Moreover, different file formats from several sequencer manufacturers can be used for the electropherogram files, thus allowing archiving sequence data from different labs from different machines. The reference sequence database, the software application, as well as any software tools can be updated online without any disturbance to the user.

BRIEF DESCRIPTION OF THE DRAWINGS

The present invention will be explained in more detail, by way of example, with reference to the drawings in which.

DETAILED DESCRIPTION OF THE PREFERRED EMBODIMENTS

Figure 1:
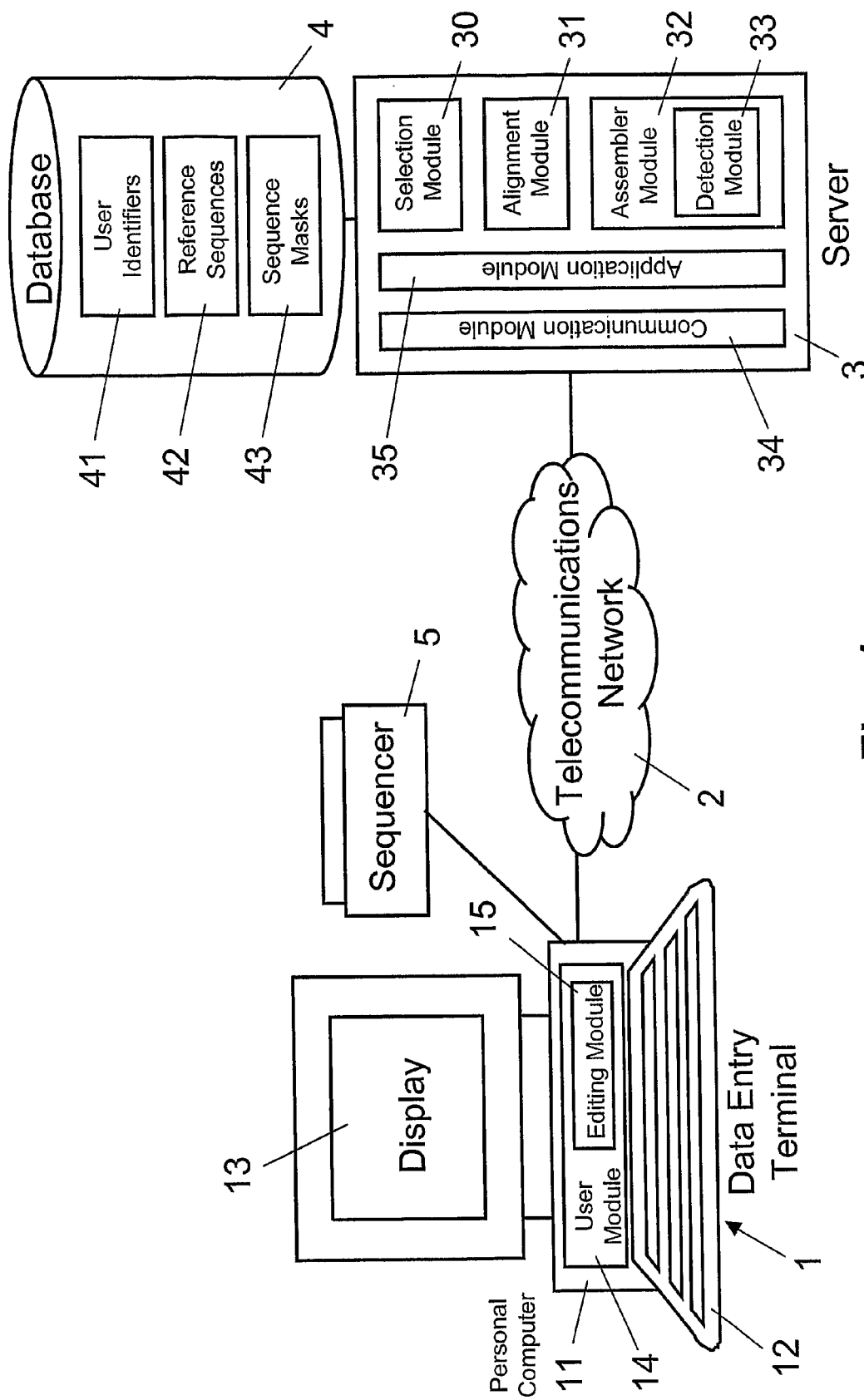
FIG. 1 shows a block diagram illustrating schematically an exemplary configuration of a computer-based system for practicing embodiments of the present invention, said configuration comprising a server with a database, and said configuration being connected to a data entry terminal via a telecommunications network.

In FIG. 1, reference numeral 1 refers to a data entry terminal. As illustrated in FIG. 1, the data entry terminal 1 includes a personal computer 11 with a keyboard 12 and a display monitor 13. As is illustrated schematically, the personal computer 11 includes a user module 14 and an editing module 15. The user module 14 and the editing module 15 are implemented as a programmed software module, for example an executable program applet that is downloaded from server 3 via telecommunications network 2.

Connected to the personal computer 11 is a conventional sequencer 5, which provides the personal computer 11 with sequence data of DNA fragments. Preferably, the fragment sequence data includes electropherograms of the DNA fragments, each electropherogram including electropherographic signals of the four nucleotide types (A, C, G, T).

As is illustrated in FIG. 1, the data entry terminal 1 is connected to server 3 through telecommunications network 2. Preferably, the telecommunications network 2 includes the Internet and/or an Intranet, making server 3 accessible as a web server through the World Wide Web or within a separate IP-network, respectively. Telecommunications network 2 may also include another fixed network, such as a local area network (LAN) or an integrated services digital network (ISDN), and/or a wireless network, such as a mobile radio network (e.g. Global System for Mobile communication (GSM) or Universal Mobile Telephone System (UMTS)), or a wireless local area network (WLAN).

As is illustrated schematically in FIG. 1, server 3 is connected to database 4. Server 3 may include one or more computers, each having one or more processors. The database 4 may be implemented on a computer shared with server 3 or on a separate computer.

The server 3 includes different functional modules, namely a communication module 34, an application module 35, a selection module 30, an alignment module 31, an assembler module 32, and a detection module 33. The communication module 35 includes conventional hardware and software elements configured for exchanging data via telecommunications network 2 with a plurality of data entry terminals 1. The application module 35 is a programmed software module configured to provide users of the data entry terminal 1 with a user interface. Preferably, the user interface is provided through a conventional Internet browser such as Microsoft Explorer or Mozilla. The selection module 30, the alignment module 31, the assembler module 32, and the detection module 33 are programmed software modules executing on a computer of server 3. Although not illustrated in FIG. 1, server 3 also includes copies of user module 14 with editing module 15 for downloading by the application module 35 to the data entry terminal 1, for execution on a processor of personal computer 11.

TABLE 1

| Reference Sequence ID | User ID | Reference Mask ID | Reference Mask Profile Information | | | |
|---|---|---|---|---|---|---|
| | | | Area of Interest ID | Description/ Name of Area of Interest | Range Start Position | Range End Position |

As is illustrated schematically in FIG. 1, database 4 includes user identifiers 41, reference sequences 42, and sequence masks 43. The user identifiers 431 are assigned to user data of registered users and/or user groups. The reference sequences 42 are stored as different sets of related reference sequences. Each set includes different variants of a specific gene sequence. The sequence masks 43 are stored assigned to the reference sequences 42. In a variant the reference sequences 42 and/or the sequence masks 43 are user specific and are stored assigned to the user identifiers 41. The sequence masks 43 include profile information related to one or more positions of the respective reference sequence. Preferably, the profile information is related to a range in the respective reference sequence. The range is defined, for example, by a start and an end position in the reference sequence or by a start position and a length (i.e. number of sequence positions). Assigned to these defined ranges, the profile information includes descriptions and/or names of specific areas of interest in the respective reference sequence. For example the areas of interest include resistance encoding positions, mismatches, ambiguities, or other special or critical zones. As is illustrated in Table 1, each reference mask may include a reference mask identifier and each area of interest may also include an area of interest identifier.

Through the user interface provided by the application module 35, the user of the data entry terminal 1 is requested to enter login information including user (or account) identifier and a password, for example. Based on the user identifiers 41 stored in the database 4, the application module 35 checks access rights of the user. Having passed the access control, the user can request the upload, from personal computer 11 to server 3, of sequence data of DNA fragments from a DNA sample, e.g. from the sequencer 5 or from another source.

For validation of DNA sequencing data, the user interface provided by the application module 35 is configured for the user to select, e.g. from a list, sequence data of one or more DNA fragments of a DNA sample, uploaded and stored previously on server 3 or in the database 4. The user is also requested through the user interface to enter a target specification identifying a target gene sequence. Subsequently, the user initiates the validation process by activating a control element such as a graphical button in the user interface provided by application module 35.

In response to the initiation received from the user through the user interface, the application module 35 activates selection module 30. The selection module 30 is configured to select and retrieve from database 4 the set of reference sequences related to the target gene sequence specified by the user. Thereafter, the selection module 30 determines for each reference sequence in the retrieved set the correlation with the previously selected sequence data of the DNA fragment of the DNA sample. For a particular reference sequence of the set, conventional pattern matching, customizable and adjustable by the user with regard to specific target requirements, is used to determine the correlation of the particular reference sequence with the selected sequence data of each DNA fragment. From the selected set of reference sequences, the selection module 30 selects the reference sequence having the highest correlation with the fragment sequence data as the selected reference sequence. For example, the gene sequence variant having the highest correlation with the sequences of the DNA fragments, defined by the fragment sequence data.

Figure 4:
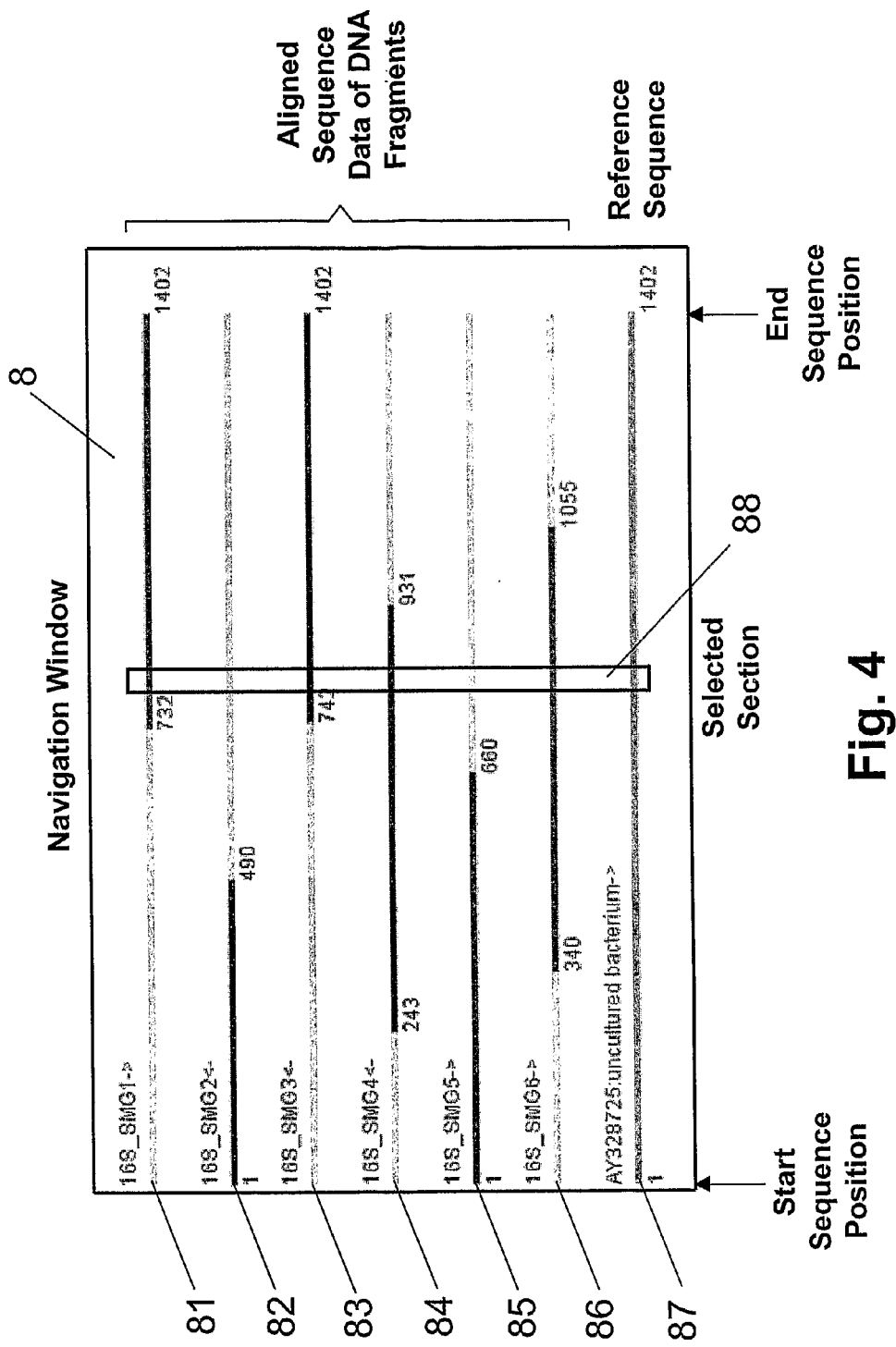
FIG. 4 shows an example of a navigation window illustrating aligned sequence data of multiple DNA fragments and reference sequence, a selected section being indicated by a frame.

After selection of the reference sequence with the highest correlation, application module 35 activates alignment module 31. The alignment module 31 aligns automatically the sequence data (i.e. the sequence) of each DNA fragment with the previously selected reference sequence. The alignment is performed with respect to optimal correlation between the selected reference sequence and the sequence of the respective DNA fragment. In FIG. 4, a navigation window 8 is shown which illustrates the alignment of the sequence data of six DNA fragments 16S-SMG1, 16S-SMG2, 16S-SMG3, 16S-SMG4, 16S-SMG5, and 16S-SMG6, with the selected reference sequence AY328725 (e.g. a particular gene sequence of an uncultured bacterium). As can be see in FIG. 4, the sequence (data) of each DNA fragment is displayed schematically on its individual line 81, 82, 83, 84, 85, 86 side by side and aligned with the schematic representation of the reference sequence on line 87. In the navigation window 8, the start position "1" as well as the end position "1402" of the reference sequence are indicated. Moreover, the start and end sequence positions of the aligned sequence (data) of each DNA fragment are indicated in the navigation window 8 (16S-SMG1: 732-1402; 16S-SMG2: 1-490; 16S-SMG3: 742-1402; 16S-SMG4: 243-931; 16S-SMG5: 1-660; and 16S-SMG6: 340-1055).

After alignment of the fragment sequence data, application module 35 activates assembler module 32. The assembler module 32 is configured to generate a contig from the aligned fragment sequence data (in a variant also from the aligned reference sequence). The contig is generated as a consensus sequence from all the fragment sequence data aligned with the selected reference sequence ((in a variant also from the selected reference sequence). The detection module 33 is invoked to identify sequence positions where nucleotide codes of aligned fragment sequence data and selected reference sequence do not correspond. If at a specific sequence position the nucleotide codes in the aligned sequence data of the DNA fragments show non-corresponding nucleotide codes, or if at a specific sequence position the nucleotide codes in the aligned sequence data of any DNA fragment have nucleotide codes that do not correspond with the nucleotide codes in the reference sequence, the detection module 33 identifies that specific sequence position as having non-corresponding nucleotide codes. Preferably, non-corresponding nucleotide codes and/or sequence positions having non-corresponding nucleotide codes are flagged. For example, for a non-corresponding nucleotide code the sequence position and, if determined, an identifier of the DNA fragment associated with the non-corresponding nucleotide code are stored assigned to the fragment sequence data. Preferably, at sequence positions where nucleotide codes in the fragment sequence data correspond to the nucleotide code in the reference sequence and at sequence positions where nucleotide codes are not present in the fragment sequence data, the assembler module 32 copies into the consensus sequence the nucleotide code of the selected reference sequence. At sequence positions identified by the detection module 33 as having non-corresponding nucleotide codes, the assembler module 32 inserts into the consensus sequence a special code indicating ambiguity, for example an IUPAC (International Union of Pure and Applied Chemistry) code.

Included in the application module 35 and in the editing module 15 is a delete function. When sections of a sequence of a DNA fragment are determined to have very low correlation with the reference sequence and/or aligned sequences of other DNA fragments (a phenomenon often observed at the two ends of a sequence), the delete function makes it possible for the user to delete selectively areas at the ends of the sequence of a DNA fragment. Information about sections deleted from sequences of DNA fragments is stored assigned to the fragment sequence data. The delete function is also performed automatically by the system for evident "trash" data at both edges of a sequence fragment, having a correlation with the reference sequence and/or aligned sequences of other DNA fragments below a defined threshold. Doing this greatly facilitates the proofreading to a user and also facilitates the automated alignments of fragments Once the contig is generated, the application module 35 creates a data set for the user. The data set includes the target specification and the fragment sequence data specified by the user, the reference sequence selected by the selection module 30, the sequence masks assigned to the selected reference sequence and user, the contig generated by the assembler module 32, and any information concerning non-corresponding nucleotide codes and/or sequence positions having non-corresponding nucleotide codes as identified by the detection module 33. The application module 35 transmits the data set and the copies of user module 14 and editing module 15 via the telecommunications network 2 to the personal computer 11 of the user. As will be explained later in more detail, the data set may also include information about user-modified nucleotide codes.

The user module 14 with the editing module 15 are installed and activated on the personal computer 11. When activated, the user module 14 controls a processor of the personal computer 11 such that it generates the graphical user interface 7 on display 13.

Figure 2:
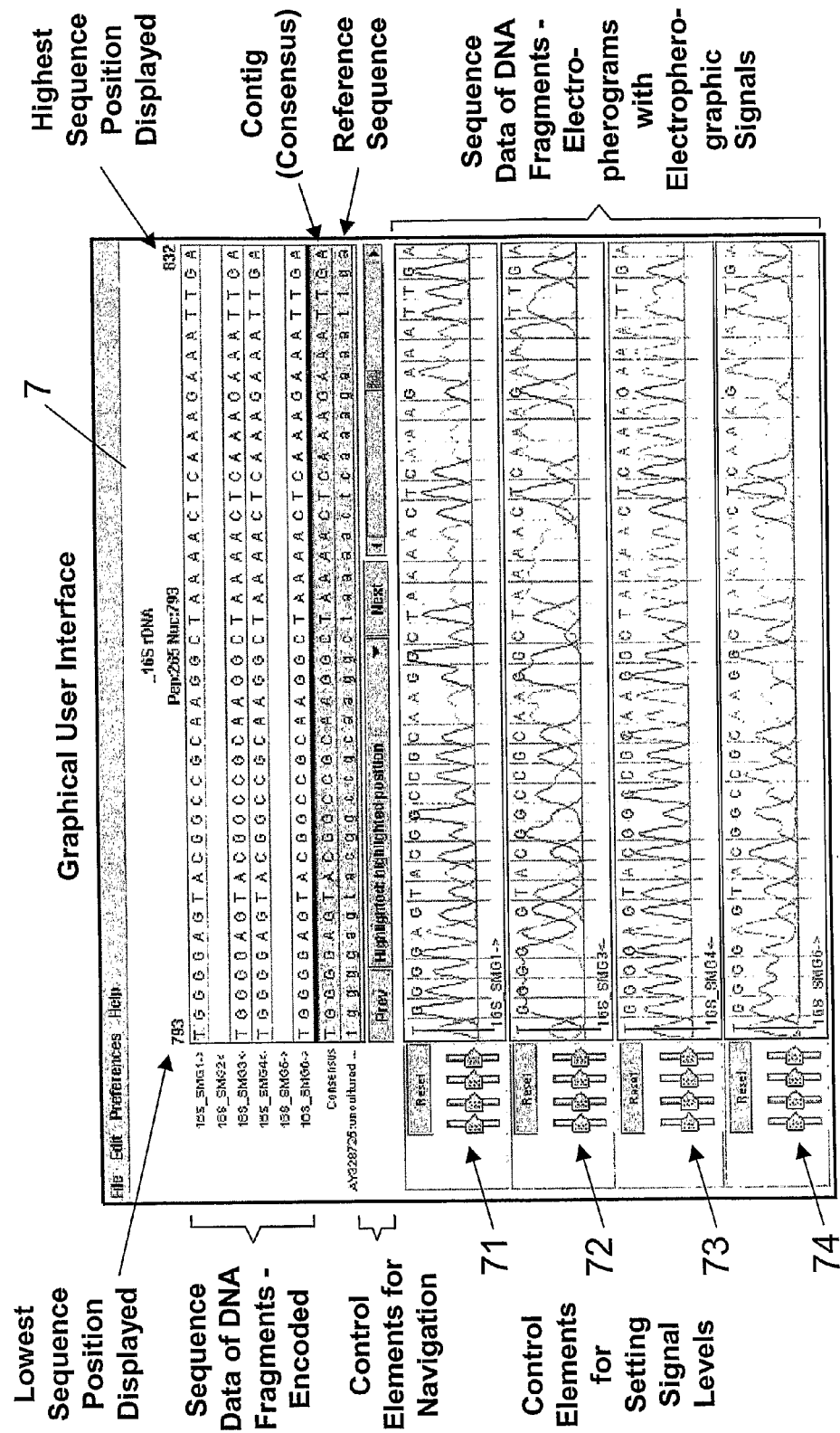
FIG. 2 shows an example of a graphical user interface for validating and editing aligned sequence data of multiple DNA fragments.

As is illustrated in FIG. 2, from the data set transmitted to the personal computer 11, the user module 14 displays in the graphical user interface 7 aligned sections (e.g. from "793", as the lowest sequence position displayed, to "832", as the highest sequence position displayed) of the sequence date of the DNA fragments, of the reference sequence, and of the contig. The sequence data of each DNA fragment is displayed along separate lines as a sequence of nucleotide codes and as an electropherographic signal. The reference sequence and the contig (consensus sequence) are displayed side by side along separate lines as a sequence of nucleotide codes. The graphical user interface 7 also includes control elements 71, 72, 73, 74 for setting the signal levels of the electropherographic signals. The control elements 71, 72, 73, 74 are associated with the electropherographic signals of each DNA fragment for adjusting the signal levels of the electropherographic signals of each nucleotide type for each DNA fragment.

As is illustrated in FIG. 2, the graphical user interface 7 includes a horizontal scroll bar for selecting the section of the aligned fragment sequence data, reference sequence, and contig to be displayed. Navigation window 8 includes a frame 88, which shows the selected section that is displayed in graphical user interface 7. By sliding the horizontal scroll bar, the selected section can be moved along the sequence positions.

Furthermore, the graphical user interface 7 includes a drop down menu for selecting areas of interest. The menu items are populated in accordance with the profile information included in the reference mask associated with the reference sequence. Every description or name of an area of interest included in the profile information is listed as a menu item in the drop down menu. When the user selects one of the items from the drop down menu, the selected section displayed of the fragment sequence data, reference sequence, and contig is adjusted to include the sequence range associated in the profile information with the selected description or name of an area of interest. If the range exceeds the number of sequence positions that can be displayed in the graphical user interface 7, the start position of the range is selected as the lowest sequence position displayed.

Figure 3:
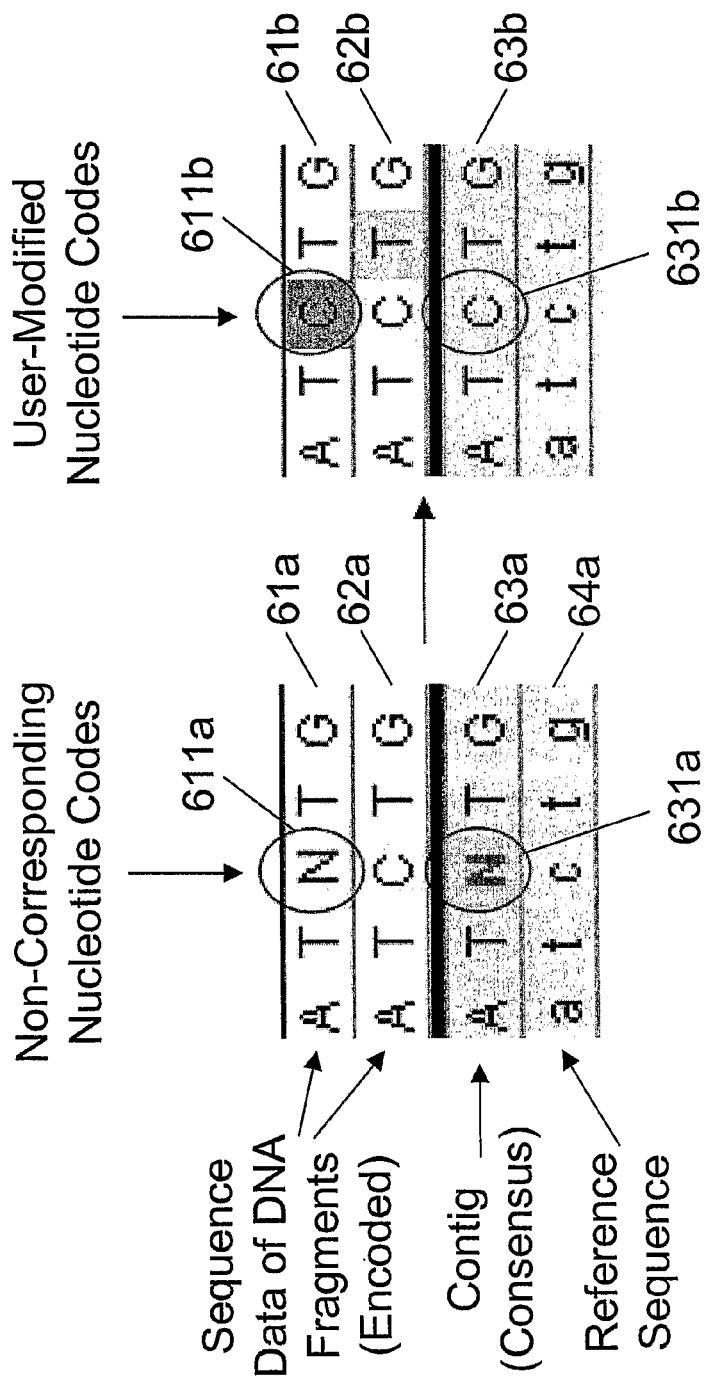
FIG. 3 shows an example of a section of aligned sequence data of DNA fragments, contig, and reference sequence, wherein non-corresponding and user modified nucleotide codes are illustrated.

Based on any information, included in the received data set, concerning non-corresponding nucleotide codes and/or sequence positions having non-corresponding nucleotide codes, the user module 14 indicates visually in the displayed section any sequence positions with non-corresponding nucleotide codes. As is illustrated in FIG. 3, sequence positions having non-corresponding nucleotide codes are highlighted by means of color or graphical symbols, for example. As can be seen in FIG. 3, the displayed section 61a of a sequence of a DNA fragment includes a different nucleotide 611a than the displayed section 62a of an aligned sequence of a DNA fragment. This ambiguity can be indicated in the displayed section 63a of the contig by means of highlighting or coloring and/or by setting nucleotide code 631a different from the code of the corresponding nucleotide of the displayed section 64a of the reference sequence.

For modification, the editing module 15 is configured to accept from the user the selection of a particular nucleotide 611b in the displayed section 61b or 62b of a sequence of a DNA fragment. For the selected nucleotide 611b, the editing module 15 receives from the user an alternative nucleotide code. The editing module 15 modifies accordingly the code of the selected nucleotide 611b. Moreover, the editing module 15 sets automatically the new nucleotide code for the corresponding nucleotide 631b in the displayed section 63b of the contig, provided that there are no further non-corresponding nucleotide codes in the fragment sequence data at that particular sequence position.

The editing module 15 is further configured to store modifications information about user-modified nucleotide codes such as sequence position, identifier of DNA fragment, previous nucleotide code, user identifier of operator responsible for modification, and date and time of modification. The modifications information includes the same information also about sections deleted from sequences of DNA fragments.

Based on the stored modification information, the user module 14 indicates visually user-modified nucleotide codes in the graphical user interface 7, for example by means of highlighting background color or a blinking attribute. Furthermore, it is possible for the user to instruct the user module 14 to display in the graphical user interface 7 user-modified sections (and corresponding reference sequence and contig), i.e. sections with fragment sequence data including at least on user-modified nucleotide code. With "next" and "previous" command buttons, the section to be displayed is moved to the next or previous user-modified section.

Once validation (proofreading and possibly correction) of the DNA sequencing data is completed by the user, the user module 14 transmits the validation data via the telecommunications network 2 to the server where it is stored by the application module 35 in database 4. The validation data includes the fragment sequence data (including any modifications), any modifications information, the contig (including any modifications), the reference sequence (or at least an identifier of the reference sequence), as well as the target specification. The application module 35 makes it also possible for a user to select and download the stored validation data, i.e. the validation data can be downloaded from the database 4 into the personal computer 11 for review and processing by means of the user module 14 and editing module 15. However, any additional modifications will result in the storage of an additional version of the validation data. The stored validation data also serves as an audit trail.

The invention claimed is:

1. A computer-implemented method of validating DNA sequencing data from fragment sequence data of one or more DNA fragments, comprising:
    obtaining from a user a target specification;
    using said fragment sequence data for said target specification to select from a set of more than one possible reference sequences stored in a database, a selected reference sequence having a highest correlation with said fragment sequence data;
    aligning automatically the fragment sequence data with the selected reference sequence using a computer;
    identifying automatically sequence positions where nucleotide codes of the aligned fragment sequence data and the selected reference sequence do not correspond; and
    using a computer in generating a contig as a consensus sequence from the fragment sequence data aligned with the selected reference sequence, the generating comprising inserting into the consensus sequence, at sequence positions having non-corresponding nucleotide codes in the fragment sequence data, a code indicating ambiguity.

2. The method according to claim 1, wherein the target specification is obtained from the user by a server via a telecommunications network, the target specification identifies a gene sequence and the selected reference sequence is selected by the server from the database from a set of one or more variants of the gene sequence.

3. The method according to claim 1, further comprising displaying side by side sections of the aligned fragment sequence data and the selected reference sequence, the fragment sequence data of each DNA fragment being displayed along a separate line; indicating visually in the sections sequence positions with non-corresponding nucleotide codes; obtaining from the user instructions to modify a nucleotide code at sequence positions having non-corresponding nucleotide codes; and modifying nucleotide codes according to the instructions obtained from the user.

4. The method according to claim 3, further comprising storing information about user-modified nucleotide codes; selectively displaying side by side modified sections of the aligned fragment sequence data and the selected reference sequence containing user-modified nucleotide codes; and indicating visually in the modified sections the user-modified nucleotide codes.

5. The method according to claim 1, further comprising storing in the database sequence masks assigned to the reference sequences, the sequence masks each including profile information related to one or more positions of the respective reference sequence; obtaining from the user interest information; and displaying side by side selected sections of the aligned fragment sequence data and the selected reference sequence, the selected sections being determined based on the interest information obtained from the user and the profile information included in the sequence mask assigned to the selected reference sequence.

6. The method according to claim 5, wherein each of the sequence masks is stored in the database assigned to a user identifier, and the selected sections are determined based on the sequence mask assigned to a user identifier obtained from the user.

7. The method according to claim 1, wherein the fragment sequence data includes electropherographic signals, the method further comprises displaying side by side sections of the aligned fragment sequence data and the selected reference sequence, the fragment sequence data of each DNA fragment being displayed along separate lines as a sequence of nucleotide codes and as an electropherographic signal, and signal levels of the electropherographic signals being adjusted individually for the different nucleotide types based on settings obtained from the user.

8. The method according to claim 1, wherein the fragment sequence data is generated by a sequencer and loaded via a telecommunications network to a server, the database is connected to the server, the fragment sequence data and the selected reference sequence are aligned by the server, the contig is generated by the server as a consensus sequence, the aligned fragment sequence data and selected reference sequence are displayed on a display terminal located at the user, instructions for setting in the contig a nucleotide code are obtained from the user through a data entry terminal located at the user, and the contig is stored by the server in a database with data including the fragment sequence data, the selected reference sequence, a user identifier obtained from the user, and information about user-modified nucleotide codes.

9. A computer-based system for validating DNA sequencing data from fragment sequence data of one or more DNA fragments, the system comprising:
    means for obtaining from a user a target specification;
    a database comprising reference sequences;
    a computer including a selection module configured to use said fragment sequence data for said target specification to select from a set of more than one possible reference sequences stored in a database, a selected reference sequence having a highest correlation with said fragment sequence data;
    an alignment module configured to align automatically the fragment sequence data with the selected reference sequence;
    a detection module configured to identify sequence positions where nucleotide codes of the aligned fragment sequence data and the selected reference sequence do not correspond; and
    an assembler module configured to generate a contig as a consensus sequence from the fragment sequence data aligned with the selected reference sequence, including to insert into the consensus sequence, at sequence positions having non corresponding nucleotide codes in the fragment sequence data, a code indicating ambiguity.

10. The system according to claim 9, wherein the means for obtaining the target specification includes a server configured to obtain the target specification from the user via a telecommunications network, the target specification identifies a gene sequence, and the selection module is located on the server and configured to select the selected reference sequence from the database from a set of one or more variants of the gene sequence.

11. The system according to claim 9, further comprising a user module configured to display side by side sections of the aligned fragment sequence data and the selected reference sequence, the fragment sequence data of each DNA fragment being displayed along a separate line and sequence positions having non-corresponding nucleotide codes, being indicated visually, the user module further being configured to obtain from the user instructions to modify a nucleotide code at sequence positions having non-corresponding nucleotide codes, and modify nucleotide codes according to the instructions obtained from the user.

12. The system according to claim 11, wherein the system further comprises means for storing information about user-modified nucleotide codes, and the user module is configured to selectively display side by side modified sections of the aligned fragment sequence data and the selected reference sequence containing user-modified nucleotide codes, and indicate visually in the modified sections the user-modified nucleotide codes.

13. The system according to claim 9, further comprising sequence masks stored in the database assigned to the reference sequences, the sequence masks each including profile information related to one or more positions of the respective reference sequence; means for obtaining from the user interest information; and a user module configured to display side by side selected sections of the aligned fragment sequence data and the selected reference sequence, the selected sections being determined based on the interest information obtained from the user and the profile information included in the sequence mask assigned to the selected reference sequence.

14. The system according to claim 13, wherein each of the sequence masks is stored in the database assigned to a user identifier, and the selected sections are determined based on the sequence mask assigned to a user identifier obtained from the user.

15. The system according to claim 9, wherein the fragment sequence data includes electropherographic signals, and the system further comprises a user module configured to display side by side sections of the aligned fragment sequence data and the selected reference sequence, the fragment sequence data of each DNA fragment being displayed along separate lines as a sequence of nucleotide codes and as an electropherographic signal, signal levels of the electropherographic signals being adjusted individually for the different nucleotide types based on settings obtained from the user.

16. The system according to claim 9, wherein the system includes a server configured to receive the fragment sequence data generated by a sequencer via a telecommunications network, the database is connected to the server, the alignment module is located on the server, and the system includes a user module configured to display the aligned fragment sequence data and the selected reference sequence on a display located at the user, the user module is configured to obtain from the user through a data entry terminal located at the user instructions for setting in the contig a nucleotide code, and the server is configured to store the contig in the database with data including the fragment sequence data, the selected reference sequence, a user identifier obtained from the user, and information about user modified nucleotide codes.

17. A computer program product comprising a non transitory computer readable medium containing therein computer program code means for controlling one or more processors of a computer-based system to perform a method for validating DNA sequencing data from fragment sequence data of one or more DNA fragments, said method including:
    obtaining from a user a target specification;
    using said fragment sequence data for said target specification to select from a set of more than one possible reference sequences stored in a database, a selected reference sequence having a highest correlation with said fragment sequence data;
    aligning automatically the fragment sequence data with the selected reference sequence using a computer;
    identifying automatically sequence positions where nucleotide codes of the aligned fragment sequence data and the selected reference sequence do not correspond; and using a computer in generating a contig as a consensus sequence from the fragment sequence data aligned with the selected reference sequence, the generating comprising inserting into the consensus sequence, at sequence positions having non-corresponding nucleotide codes in the fragment sequence data, a code indicating ambiguity.

18. The computer program product according to claim 17, wherein in such method a server of the system obtains from the user the target specification, and identifies a gene sequence via a telecommunications network and the server selects the selected reference sequence from the database from a set of one or more variants of the gene sequence.

19. The computer program product according to claim 17, wherein in such method the system displays side by side sections of the aligned fragment sequence data and the selected reference sequence, the fragment sequence data of each DNA fragment being displayed along a separate line, indicates visually in the sections sequence positions with non-corresponding nucleotide codes, obtains from the user instructions to modify a nucleotide code at sequence positions having non corresponding nucleotide codes, and modifies nucleotide codes according to the instructions obtained from the user.

20. The computer program product according to claim 19, wherein in such method the system stores information about user-modified nucleotide codes, selectively displays side by side modified sections of the aligned fragment sequence data and the selected reference sequence containing user-modified nucleotide codes, and indicates visually in the modified sections the user-modified nucleotide codes.

21. The computer program product according to claim 17, wherein in such method the system stores in the database sequence masks assigned to the reference sequences, the sequence masks each including profile information related to one or more positions of the respective reference sequence, obtains from the user interest information; and displays side by side selected sections of the aligned fragment sequence data and the selected reference sequence, the selected sections being determined based on the interest information obtained from the user and the profile information included in the sequence mask assigned to the selected reference sequence.

22. The computer program product according to claim 21, wherein in such method the system stores each of the sequence masks in the database assigned to a user identifier, and determines the selected sections based on the sequence mask assigned to a user identifier obtained from the user.

23. The computer program product according to claim 17, wherein in such method the system displays side by side sections of the aligned fragment sequence data and the selected reference sequence, the fragment sequence data of each DNA fragment being displayed along separate lines as a sequence of nucleotide codes and as an electropherographic signal, signal levels of the electropherographic signals being adjusted individually for the different nucleotide types based on settings obtained from the user.

24. The computer program product according to claim 17, wherein in such method a server of the system receives the fragment sequence data generated by a sequencer via a telecommunications network, the server aligns the fragment sequence data and the selected reference sequence; the server generates the contig as a consensus sequence, a display of the system located at the user displays the aligned fragment sequence data and the selected reference sequence, a data entry terminal located at the user obtains instructions for setting in the contig a nucleotide code, and the server stores the contig in a database with data including the fragment sequence data, the selected reference sequence, a user identifier obtained from the user, and information about user-modified nucleotide codes.

* * * * *